United States Patent [19]

Clausen et al.

[11] Patent Number: 5,068,191
[45] Date of Patent: Nov. 26, 1991

[54] PURIFIED HISTO-BLOOD GROUP A GLYCOSYLTRANSFERASE AND ANTIBODIES THERETO

[75] Inventors: Henrik Clausen; Fumi-ichiro Yamamoto; Thayer White; Sen-itiroh Hakomori, all of King County, Wash.

[73] Assignee: The Biomembrane Institute, Seattle, Wash.

[21] Appl. No.: 402,695

[22] Filed: Aug. 31, 1989

[51] Int. Cl.[5] .................... C12N 9/12; C12N 5/02; A61K 35/14; C12P 21/08
[52] U.S. Cl. .................... 435/193; 435/183; 435/240.26; 435/240.27; 530/386; 530/387; 530/395; 935/89; 935/95; 935/96; 935/99; 935/102; 935/103; 935/106
[58] Field of Search ............ 435/7, 183, 193, 240.26, 435/240.27, 7.1, 7.2; 530/387, 386, 808, 809, 394, 395; 935/89, 95, 96, 99, 102, 103, 106

[56] References Cited

OTHER PUBLICATIONS

Childs et al., "Blood-group-related carbohydrate antigens are expressed on human milk galactosyltransferase and are immunogenic in rabbits," *Biochem. J.* 238:605-611 (1986).

Clausen et al., "Monoclonal Antibodies Defining Blood Group A Variants with Difucosyl Type 1 Chain (ALe$^b$) and Difucosyl Type 2 Chain (ALe$^y$)," *Biochemistry* 24:6190-6194 (1985).

Clausen et al., "Further Characterization of Type 2 and Type 3 Chain Blood Group A Glycosphingolipids from Human Erythrocyte Membranes," *Biochemistry* 25:7075-7085 (1986).

Clausen et al., "Incompatible A Antigen Expressed in Tumors of Blood Group O Individuals: Immunochemical, Immunohistologic, and Enzymatic Characterization," *J. Immunol.* 136:326-330 (1986).

Cook et al., "A rabbit antibody to the blood-group-A-gene-specified a-3-N-acetylgalactosaminyltransferase," *Bio-chem. Soc. Trans.* 10:446-447 (1982).

Greenwell et al., "Approaches to cloning the genes at the human blood group ABO locus," *Biochem. Soc. Trans.* 15:601-603 (1987).

Nagai et al., "Human Blood Group Glycosyltransferases," *J. Biol. Chem.* 253:377-379 (1978).

Roth et al., "Differential Subcompartmentation of Terminal Glycosylation in the Golgi Apparatus of Intestinal Absorptive and Goblet Cells," *J. Biol. Chem.* 261:14307-14312 (1986).

Schwyzer et al., "Porcine A Blood Group-specific N-Acetylgalactosaminyltransferase," *J. Biol. Chem.* 225:2346-2355 (1977).

Taatjes et al., "Post-Golgi Apparatus Localization and Regional Expression of Rat Intestinal Sialyltransferase Detected by Immunoelectron Microscopy with Polypeptide Epitope-purified Antibody," *J. Biol. Chem.* 263:6302-6309 (1988).

Takizawa et al., "Immunological Specificity of Blood Group Glycosyltransferase," in T. Yamakawa, T. Osawa and S. Handa (eds.), *Glycoconjugates*, Japanese Scientific Societies Press, Tokyo, 1981, pp. 379-380.

Topping et al., "Isoelectric Points of the Human Blood Group A$^1$, A$^2$ and B Gene-Associated Glycosyltransferases in Ovarian Cyst Fluids and Serum," *Biochem. Biophys. Res. Commun.* 64:89-96 (1975).

(List continued on next page.)

Primary Examiner—Robert A. Wax
Assistant Examiner—Stephanie W. Zitomer
Attorney, Agent, or Firm—Seed and Berry

[57] ABSTRACT

The genes defining the ABO histo-blood groups are disclosed. Methods for identification of histo-blood group ABO status are provided. The methods include the use of DNA probes or size separation of DNA fragments unique to a blood group status. The present invention also discloses DNA constructs, recombinant methods for providing histo-blood glycosyltransferases, methods for tumor suppression, purified histo-blood group glycosyltransferases, and antibodies produced therefrom which bind to protein epitopes.

8 Claims, 5 Drawing Sheets

OTHER PUBLICATIONS

Tuppy et al., "Microsomal Incorporation of N-Acetyl-D-Galactosamine into Blood Group Substance," *Nature* 210:316–317 (1966).

Watkins et al., "Specific Inhibition Studies Relating to the Lewis Blood-Group System," *Nature* 180:1038–1040 (1957).

Watkins et al., "Possible Genetical Pathways for the Biosynthesis of Blood Group Mucopolysaccharides," *Vox Sang.* 4:97–119 (1959).

Whitehead et al., "An N-acetylgalactosaminyl-transferase from Human Blood Group A Plasma," *J. Biol. Chem.* 249:3442–3447 (1974).

Yoshida et al., "Immunologic Homology of Human Blood Group Glycosyltransferases and Genetic Background of Blood Group (ABO) Determination," *Blood* 54:344–350 (1979).

Yoshida, "Identification of Genotypes of Blood Group A and B," *Blood* 55:119–123 (1980).

FIG. 1 a.

```
                        5                    10                        15
      (Lys)asp Glu Gly his  Phe Tyr Tyr Leu Gly Gly Phe Phe Gly Gly
                              5'                                3'
          Oligo FY-1:    TTC TAC TAC CTG GGA GGA TTC TTC GG
                           T   T   T   C   C   C   T   T
                                           T   T
```

```
                        20                   25
            Ser Val Gln Glu Val Gln Arg Leu Thr Arg Ala gln
                                                        cys
              5'                  3'
       FY-3: GTG CAG GAG GTG CAG AG
              A   A   A   A   A C
              C           C
              T           T
```

```
                        30                   35                   40
       xxx Gln Ala Met Met Val Asp Gln Ala asn Gly Ile Glu Ala Val
                T                   T
            T   A               C A T A
           GTC CGG TAC TAC CAG CTG GTC CGG TTG CC  : FY-2
           3'                                   5'
``` b.      c.

```
  1 ATG GCC GAG GTG TTG CGG ACG CTG GCC GGA AAA CCA AAA TGC CAC
  1 met ala glu val leu arg thr leu ala gly lys pro lys cys his 46 GCA CTT CGA CCT ATG ATC CTT TTC CTA ATA ATG CTT GTC TTG GTC
 16 ala leu arg pro met ile leu phe leu ile met leu val leu val
        <========== possible transmembrane domain ==========
 91 TTG TTT GGT TAC GGG GTC CTA AGC CCC AGA AGT CTA ATG CCA GGA
 31 leu phe gly tyr gly val leu ser pro arg ser leu met pro gly
    ==========================>
136 AGC CTG GAA CGG GGG TTC TGC ATG GCT GTT AGG GAA CCT GAC CAT
 46 ser leu glu arg gly phe cys met ALA val arg glu pro asp his
                                    <-- --- --- --- --- --- ---
181 CTG CAG CGC GTC TCG TTG CCA AGG ATG GTC TAC CCC CAG CCA AAG
 61 leu gln arg val ser leu pro arg met val tyr pro gln pro lys
    --- --- M-9/K-4 --- --- --- --- --- --- --- --- --- xxx <->
226 GTG CTG ACA CCG TGG AAG GAT GTC CTC GTG GTG ACC CCT TGG CTG
 76 val leu thr pro TRP lys ASP val leu val val thr pro trp leu
    --- K-1 --- --cys xxx<-> arg --- K-9 --- --- --- -->
271 GCT CCC ATT GTC TGG GAG GGC ACA TTC AAC ATC GAC ATC CTC AAC
 91 ala pro ile val trp glu gly thr phe asn ile asp ile leu asn 316 GAG CAG TTC AGG CTC CAG AAC ACC ACC ATT GGG TTA ACT GTG TTT
106 glu gln phe arg leu gln ASN thr thr ile gly leu thr val phe 361 GCC ATC AAG AAA TAC GTG GCT TTC CTG AAG CTG TTC CTG GAG ACG
121 ala ile lys lys tyr val ala phe leu lys leu phe leu glu thr 406 GCG GAG AAG CAC TTC ATG GTG GGC CAC CGT GTC CAC TAC TAT GTC
136 ala glu lys HIS phe met val gly his arg val his tyr tyr val
                <-- ASP --- --- --- --- K-5/M-7 --- --- --- ---
451 TTC ACC GAC CAG CTG GCC GCG GTG CCC CGC GTG ACG CTG GGG ACC
151 phe thr asp gln LEU ala ala val pro arg val thr leu gly thr
    --- --- --- --- PRO --- --- --- --- --- --- --- --- --- ---
496 GGT CGG CAG CTG TCA GTG CTG GAG GTG CGC GCC TAC AAG CGC TGG
166 gly arg gln leu ser val leu glu val arg ala tyr lys arg trp
    --- --- --- --- --- --- --- --- --- --- --- --- --- -->
541 CAG GAC GTG TCC ATG CGC CGC ATG GAG ATG ATC AGT GAC TTC TGC
181 gln asp val ser met arg arg met glu met ile ser asp phe cys
```

FIG. 3

```
                                                        <--  ---  ---  M-8  ---  ---
586 GAG CGG CGC TTC CTC AGC GAG GTG GAT TAC CTG GTG TGC GTG GAC
196 glu arg arg phe leu ser glu val asp tyr leu val cys val asp
    ---  ---  ---  ---  ---  ---  ---  ---  ---  ---  ---  ---  ---  ---  -->
631 GTG GAC ATG GAG TTC CGC GAC CAC GTG GGC GTG GAG ATC CTG ACT
211 val asp met glu phe arg asp his val gly val glu ile leu thr 676 CCG CTG TTC GGC ACC CTG CAC CCC GGC TTC TAC GGA AGC AGC CGG
226 pro leu phe gly thr leu his pro gly phe tyr gly ser ser arg 721 GAG GCC TTC ACC TAC GAG CGC CGG CCC CAG TCC CAG GCC TAC ATC
241 glu ala phe thr tyr glu arg arg pro gln ser gln ala tyr ile 766 CCC AAG GAC GAG GGC GAT TTC TAC TAC CTG GGG GGG TTC TTC GGG
256 pro lys asp glu gly ASP phe tyr tyr leu gly gly phe phe gly
                        <--  ---  ---  ---  his  ---  K-8  ---  ---  ---  ---  ---  ---  ---
811 GGG TCG GTG CAA GAG GTG CAG CGG CTC ACC AGG GCC TGC CAC CAG
271 gly ser val gln glu val gln arg leu thr arg ala cys his gln
    ---  ---  ---  ---  ---  ---  ---  ---  ---  ---  ---  ---  ---  xxx  ---
856 GCC ATG ATG GTC GAC CAG GCC AAC GGC ATC GAG GCC GTG TGG CAC
286 ala met met val asp gln ala asn gly ile glu ala val trp his
    ---  ---  ---  ---  ---  ---  ---  ---  ---  ---  ---  ---  -->
901 GAC GAG AGC CAC CTG AAC AAG TAC CTG CTG CGC CAC AAA CCC ACC
301 asp glu ser his leu asn lys tyr leu leu arg his lys pro thr
                            <--  ---  ---  K-2  ---  ---  ---  ---  ---
946 AAG GTG CTC TCC CCC GAG TAC TTG TGG GAC CAG CAG CTG CTG GGC
316 lys val leu ser pro glu tyr leu trp asp gln gln leu leu gly
    <->  ---  K-7  ---  ---  ---  ---  ---  ---  ---  ---  xxx  ---  ---  ---
991 TGG CCC GCC GTC CTG AGG AAG CTG AGG TTC ACT GCG GTG CCC AAG
331 trp pro ala val leu arg lys leu arg phe thr ala val pro lys
    ---  ---  ---  ---  ---  xxx  <->  ---  ---  K-3  ---  ---  ---  ---  -->
1036 AAC CAC CAG GCG GTC CGG AAC CCG TGA
346  asn his gln ala val arg asn pro ---
```

PURIFIED HISTO-BLOOD GROUP A GLYCOSYLTRANSFERASE AND ANTIBODIES THERETO

TECHNICAL FIELD

The present invention relates generally to the ABO histo-blood groups. This invention is more particularly related to the genes defining the ABO histo-blood groups, probes to the DNA sequences, methods for identification of histo-blood group ABO status, methods for tumor suppression, DNA constructs, recombinant plasmids, recombinant methods for producing histo-blood glycosyltransferases, purified histo-blood glycosyltransferases and antibodies produced therefrom which bind to protein epitopes.

BACKGROUND OF THE INVENTION

The histo-blood group ABH determinants are major alloegeneic antigens in both erythrocytes and tissues of humans. They generally constitute peripheral parts of the oligosaccharide chains of glycoconjugates, i.e., linked to lipids (glycosphingolipids) or to proteins (glycoproteins). The structure of the antigen determinants was established in the 1950s by Watkins and Morgan (*Nature* 180:1038-1040, 1957) and Kabat et al. (Blood Group Substrates: Their Chemistry and Immunochemistry. 1956, Academics Press, New York). Subsequently, Watkins and Morgan (*Vox Sang.* 4:97-119, 1959) proposed that the A and B phenotypes were associated with glycosyltransferases that converted the H substance associated with 0 phenotype to A and B, respectively, through the addition of $\alpha 1 \to 3$-N-acetylgalactosamine or $\alpha 1 \to 3$-galactosyl residues to H antigen, Fuc$\alpha 1 \to 2$Gal$\beta 1 \to$R. Thus, the primary products of the histo-blood group A and B genes are the respective glycosyltransferases.

At present, knowledge of the histo-blood group antigens is limited to their chemistry, immunology, biosynthesis and genetic inheritance. DNA sequence information for the ABO genes has not been available, due primarily to the difficulty associated with purifying mammalian glycosyltransferases in sufficient quantities. Nucleotide probes based on amino acid sequence information of the A and B transferase proteins would allow cloning and characterization of the ABO genes, and thereby permit methods for direct DNA blood grouping.

Consequently, there exists a need in the art for purified histo-blood group A or B glycosyltransferase and the primary structure of the genes encoding them. The present invention fills this need, and further provides other related advantages.

SUMMARY OF THE INVENTION

Briefly stated, the present invention provides a substantially pure histo-blood group A glycosyltransferase. The protein may be derived from human cells.

Within a related aspect, the present invention discloses antibodies that bind to protein epitopes on histo-blood group A glycosyltransferases. Particularly preferred monoclonal antibodies include WKH-1, produced by a hybridoma designated by ATCC No. HB 10207.

In another aspect of the present invention, an isolated DNA molecule encoding a histo-blood group A glycosyltransferase is disclosed. Within one embodiment, the DNA sequence encodes the amino acid sequence shown in FIG. 3 from glutamic acid, amino acid number 57, to proline, amino acid number 353. In another embodiment, the DNA sequence encodes the amino acid sequence shown in FIG. 3 from alanine, amino acid number 2, to proline, amino acid number 353. Also disclosed is an isolated DNA molecule capable of specifically hybridizing with a DNA molecule encoding a histo-blood group A glycosyltransferase.

Within a related aspect of the present invention, an isolated DNA molecule encoding a histo-blood group B glycosyltransferase and an isolated DNA capable of specifically hybridizing with a DNA molecule encoding a histo-blood group B glycosyltransferase are disclosed. The present invention also discloses both an isolated DNA molecule encoding a protein of a histo-blood group O gene and an isolated DNA molecule capable of specifically hybridizing with a DNA molecule encoding a protein comprising a product of a histo-blood group O gene.

In another aspect of the present invention, methods are provided for detecting histo-blood group ABO status. In one embodiment, the method comprises: isolating DNA from a patient; incubating the DNA with at least two DNA probes under conditions permitting hybridization, wherein one of the probes comprises a nucleotide sequence derived from DNA encoding histo-blood group A glycosyltransferase, or portion thereof, and another of the probes comprises a nucleotide sequence derived from DNA encoding histo-blood group B glycosyltransferase; and detecting the presence or absence of a pattern of hybridization of the DNA with the DNA probes, and therefrom determining the histo-blood group ABO status. In another embodiment, the method comprises: isolating DNA from a patient; incubating a first aliquot of the DNA with a DNA probe comprising a nucleotide sequence derived from DNA encoding for histo-blood group A glycosyltransferase, or portion thereof, under conditions permitting hybridization; incubating a second aliquot of the DNA with a DNA probe comprising a nucleotide sequence derived from DNA encoding for histo-blood group B glycosyltransferase, or portion thereof, under conditions permitting hybridization; and detecting the presence or absence of a pattern of hybridization and therefrom determining the histo-blood group ABO status. In yet another embodiment, the method comprises: isolating DNA from a patient; cleaving the DNA with at least one restriction endonuclease to produce two or more DNA fragments; separating the DNA fragments by size; and detecting the presence of DNA fragments unique to histo-blood group A, or B or 0 status, and therefrom determining histo-blood group ABO status.

Within a related aspect, DNA constructs comprising a DNA sequence encoding histo-blood group A glycosyltransferase and plasmids comprising the DNA sequence, are disclosed. Suitable promoters and/or polyadenylation signals are also disclosed. In addition, cells transfected with the DNA constructs, and methods for producing histo-blood group A glycosyltransferase using host cells transfected or transformed with a suitable DNA construct are also disclosed. A method for producing A glycosyltransferase comprises: introducing into a host cell an isolated DNA molecule encoding a histo-blood group A glycosyltransferase, or a DNA construct comprising a DNA sequence encoding histo-blood group A glycosyltransferase; growing the host cell in an appropriate medium; and isolating the protein product encoded by the DNA construct produced by the host cell. Similarly, DNA constructs comprising a DNA sequence encoding histo-blood group B glycosyltransferase, plasmids therefrom, and methods for recombinant production of the B glycosyltransferase from an isolated DNA molecule or a DNA construct, are disclosed.

In yet another aspect of the present invention, methods for suppressing tumor growth in a patient are disclosed. The methods generally comprise: establishing a nonpathogenic bacterial cell which contains a DNA sequence encoding histo-blood group A glycosyltransferase; and introducing the bacterial cell into the intestinal tract of a patient, thereby enriching the bacterial flora to A antigen, wherein the enrichment stimulates a humeral immune response to the tumor.

These and other aspects of the present invention will become evident upon reference to the following detailed description and drawings.

BRIEF DESCRIPTION OF THE DRAWINGS

FIG. 1a depicts a partial amino acid sequence of the internal peptide (K-8) and corresponding degenerate oligodeoxynucleotide sequences used as primers and probes. N-terminal amino acid sequence information (42 a.a.) used for the PCR experiment is shown in bold type. The oligonucleotide sequences of primers FY-1 and FY-2, and probe FY-3, are presented beneath the amino acid sequences of the respective regions. In order to decrease degeneracy, rarely used codons were omitted from the synthesis of FY-1 and FY-2. The degeneracy of these three oligos are 576 (FY-1), 144 (FY-2), and 256 (FY-3), respectively.

FIG. 1b represents the results of a PCR presence test. The nucleotide sequence between oligos FY-1 and FY-2 in genomic and cDNA were amplified by the PCR method and analyzed by polyacrylamide gel/electroblot. Radiolabeled FY-3 oligo probe was used for hybridization. The DNAs tested were: (lane 1) genomic DNA from blood type A individual, (2) B individual, (3) O individual, and (4) random-primed MKN45 cDNA. The positions of marker fragments from phi $\times$174/Hae III (118 bp and 72 bp) are indicated by arrows.

FIG. 1c represents the results of PCR identification. DNAs from 6 phage candidates (lanes 5–10) were analyzed for the presence of the nucleotide sequence between oligos FY-1 and FY-2 as per the presence test. In lane 11, the 98 bp fragment from the presence test of MKN45 cDNA was gel-purified and used as a control size marker.

FIG. 3 depicts the amino acid sequence of human A transferase inferred from the nucleotide sequence of cDNA clone FY-59-5. Alanine at a.a. 54 of the N-terminal portion of the soluble enzyme, and a possible N-glycosylation site (Asn at a.a. 112) are indicated in bold type. The positions and the names of the peptide fragments which were sequenced are shown by broken lines (e.g., ←K-1→). The mismatches between the deduced and sequenced amino acids are indicated by bold type. The small letters represent ambiguous amino acids and the symbol xxx represents undetermined amino acids. The apparent transmembrane domain is also indicated.

FIG. 4 depicts a comparison of nucleotide sequences among ABO alleles. The nucleotide sequences of a representative O allelic cDNA clone (FY-65-O) and a representative B allelic cDNA clone (FY-66-B) are compared with the nucleotide sequence of the representative A allelic cDNA clone (FY-59-A) whose sequence is depicted in FIG. 3. The nucleotide differences are indicated by the position number and nucleotide symbol. The position numbers correspond with those found in FIG. 3. Inversions ($\underline{V}$) and deletions (-v-) are also indicated.

DETAILED DESCRIPTION OF THE INVENTION

Prior to setting forth the invention, it may be helpful to an understanding thereof to set forth definitions of certain terms to be used herein.

Antibody—as used herein, includes an intact molecule, a fragment thereof, or a functional equivalent thereof; and may be genetically engineered. Examples of antibody fragments include F(ab')$_2$, Fab', Fab and Fv.

Complementary DNA or cDNA—a DNA molecule or sequence which has been enzymatically synthesized from the sequences present in an mRNA template, or a clone of such a molecule.

DNA Construct—a DNA molecule, or a clone of such a molecule, either single- or double-stranded, which has been modified to contain segments of DNA which are combined and juxtaposed in a manner which would not otherwise exist in nature.

Plasmid or Vector—a DNA construct containing genetic information which may provide for its replication when inserted into a host cell. A plasmid generally contains at least one gene sequence to be expressed in the host cell, as well as sequences which facilitate such gene expression, including promoters and transcription initiation sites. It may be a linear or closed circular molecule.

The present invention provides the histo-blood group A glycosyltransferase. This protein, also known as UDP-GalNAc:Fuc$\alpha$1→2Gal$\alpha$1→3GalNAc transferase, catalyzes the transfer of $\alpha$1→3GalNAc to substrates such as Fuc$\alpha$1→2Gal$\beta$1→R (H antigen).

Histo-blood group A glycosyltransferase may be isolated by a combination of extraction and chromatography techniques. Briefly, in one embodiment, enzyme activity is extracted from mammalian cells by homogenization and solubilization with detergent. The detergent extract is passed over a gel filtration column. Fractions containing enzyme activity are further purified by cation exchange chromatography. Final purification is performed using reverse-phase column chromatography.

A variety of body fluids and tissues, such as plasma, kidney and lung, are suitable for purification of histo-blood group A transferase. A preferred source of starting material for such purification is human cells. A representative isolation procedure is as follows. Homogenization of tissue in a buffer solution containing a detergent such as Triton X-100 yields a solution with constant A transferase activity. The soluble supernatant of the extract may be adsorbed on Sepharose 4B and eluted with UDP. The ability of Sepharose 4B to adsorb A transferase, and elution of the enzymatic activity, appear to be lot-dependent. The selectivity of the binding to Sepharose may be shown by the specific elution with UDP and not GDP, UMP or 0.2M NaCl. Further purification of the enzyme is accomplished by cation exchange chromatography, e.g., by application of a diluted and pH-adjusted Sepharose 4B eluate to a mono-S HR 5/5 column (Pharmacia LKB, Upsala, Sweden). Where it is desired to combine and concentrate single enzyme preparations, a second cation exchange chromatography step may be utilized. Final purification of the histo-blood group A transferase to homogeneity is achieved by reverse phase chromatography, e.g., by application of a diluted and pH-adjusted cation exchange eluate to a proRPC H5/10 column.

A representative purified histo-blood group A transferase of the present invention has the following characteristics. Sodium dodecyl sulfate polyacrylamide gel electrophoresis (SDS-PAGE) shows a single protein band with apparent molecular weight (MW) of approximately 40,000 under both reducing and nonreducing conditions. The 40,000MW band is the only band to increase with the increases in specific activity associated with the steps in the purification process, and the band is absent in extracts of tissue from O individuals. Digestion with N-glycanase results in a reduction in MW of about 6,000 (as estimated by SDS-PAGE), indicating that the A transferase is a glycoprotein with at least one N-linked carbohydrate chain. The amino acid composition and partial amino acid sequence was determined for the purified A transferase.

The present invention also provides antibodies that bind to histo-blood group A transferase. The antibodies are useful tools for the cytolocalization, e.g., by immuno-gold electron microscopy, of glycosyl-transferases and for elucidating their role in cellular differentiation and malignant transformation. The purified native histo-blood group A transferase protein described above may be utilized to produce polyclonal or monoclonal antibodies which bind to the A transferase protein. It will be evident to one skilled in the art that antibodies to fragments of A transferase or to intact, denatured A transferase may also be produced. The latter type of antibodies are particularly useful for detection of "fixed," e.g., formaldehyde or glutaraldehyde, cells expressing A transferase.

Briefly, polyclonal antibodies may be produced by immunization of an animal and subsequent collection of its sera. It is generally preferred to follow the initial immunization with one or more boosters prior to sera collection.

Monoclonal antibodies (MAbs) may be generally produced by the method of Kohler and Milstein (*Nature* 256:495–497, 1975; *Eur. J. Immunol.* 6:511–519, 1976). Briefly, the lymph nodes and/or spleens of an animal injected with purified protein are fused with myeloma cells to form hybrid cell lines ("hybridomas" or "clones"). Each hybridoma secretes a single type of immunoglobulin specific for the protein, and, like the myeloma cells, has the potential for indefinite cell division.

The MAbs of the present invention are produced by immunization of an animal with substantially pure histo-blood group A transferase. Spleen cells are fused with myeloma cells and hybridomas cloned by limiting dilution procedures. Hybridomas may be selected on the basis of reactivity with the purified native A transferase protein which is attached to a solid phase, staining of blood group A cells possessing high A transferase activity, and immunoprecipitation of transferase activity. This strategy for screening hybridomas allows for the selection of "functional" antibodies, i.e., ones capable of immunoprecipitating and inhibiting transferase activity. An additional screening for the absence of reactivity with blood group ABH carbohydrate determinants permits the selection of hybridomas secreting MAbs directed to protein epitopes associated with the A transferase, but not its immunodominant ABH carbohydrate determinants.

A representative MAb, WKH-1, is produced by a hybridoma designated by ATCC No. HB 10207. The MAb reacts with cells having high A transferase activity and immunoprecipitates the A transferase activity as well as iodinated 40,000MW iodinated transferase protein. The MAb immunoprecipitates and partially inhibits not only $A_1$ and $A_2$, but also B transferase activity, and reacts with B cells expressing B transferase, thus indicating a cross-reactivity with B transferase. In contrast, the MAb has shown no reactivity with various cells having the O phenotype. It will be evident to those skilled in the art that other MAbs, including ones that competitively inhibit the formation of an immunocomplex between WKH-1 and histo-blood group A transferase, may be produced.

The present invention also provides isolated DNA molecules, including genomic DNA and cDNA, encoding histo-blood group A transferase. Based on the partial amino acid sequence of the purified A transferase, the cDNA encoding this protein was cloned. The cloning strategy may be briefly summarized as follows: 1) synthesis of degenerate oligodeoxynucleotides reverse translated from amino acid sequence; 2) cDNA preparation; 3) polymerase chain reaction (PCR) presence test; 4) preparation of amplified fragment; 5) cDNA library construction; 6) PCR presence test for amplified cDNA library (optional); 7) screening the library with amplified fragment probe; and 8) PCR identification test. More specifically, for the isolation of a representative DNA molecule encoding a histo-blood group A glycosyltransferase, poly A+ RNA from the human stomach cancer cell line MKN45 (which expresses high levels of A-antigen) was used for construction of a λgt10 cDNA library. Alternatively, a cDNA library has been constructed from human tissue. Degenerate synthetic oligodeoxynucleotides were used for polymerase chain reactions to detect the presence of the sequence of interest in cDNA (presence test), and to identify the correct clones (identification test) after screening the library with a radiolabeled PCR amplified fragment.

Figure 1:
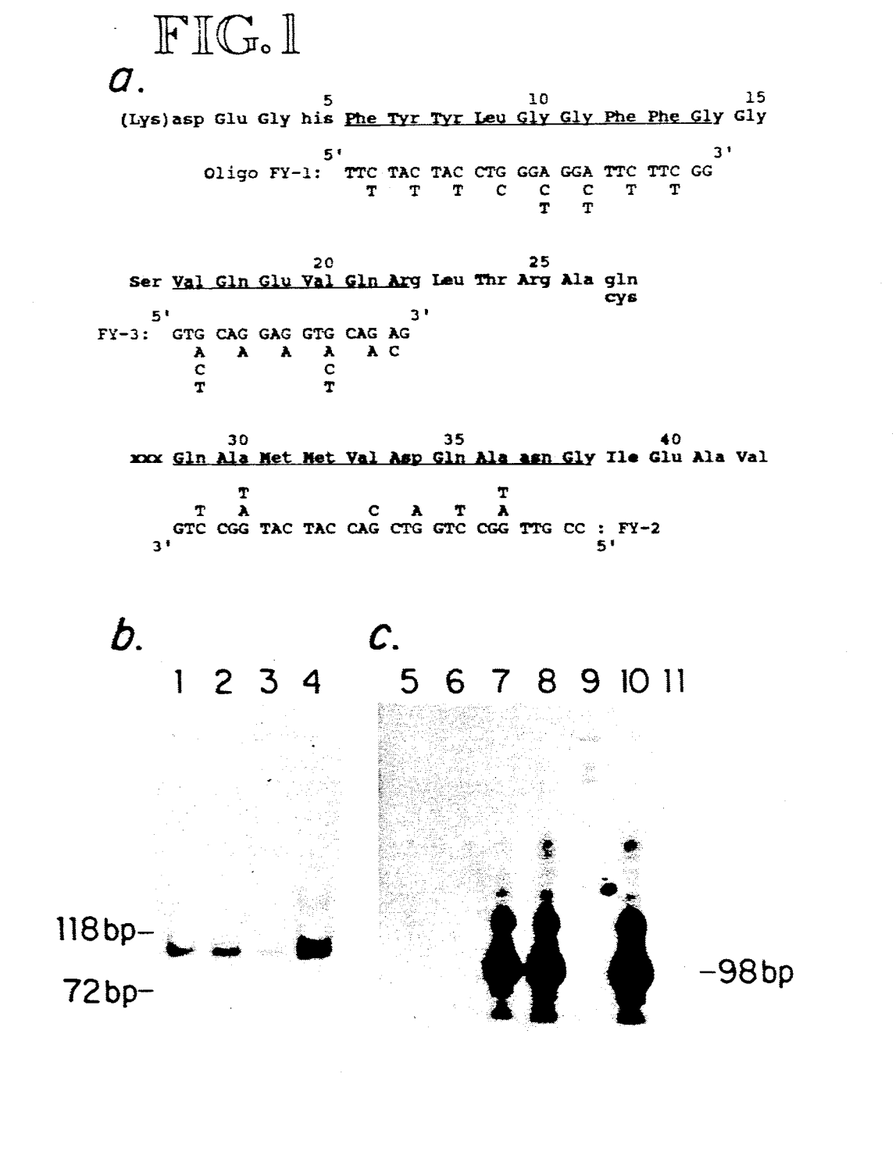
FIG. 1 depicts the cloning of A glycosyltransferase.

Oligonucleotide probes based on the partial amino acid sequences of A transferase protein were constructed as shown in FIG. 1a. cDNA was constructed by random-priming, and PCR analysis was used to ascertain whether the sequence of interest was present in the cDNA (presence test). As shown in FIG. 1b, we obtained a 98 bp fragment of the expected size as detected by FY-3 oligomer probe for the internal sequence of the amplified fragment. Subsequently, this fragment was gel-purified and used to screen the cDNA library after $^{32}$P-labeling in a PCR reaction. Stringent hybridization and washing conditions were employed (e.g., Suggs et al. in *Developmental Biology Using Purified Genes.* eds. D. Brown and C. F. Fox, p. 683, Academic Press, N.Y., 1981). Identity of the candidate clones was tested by PCR (identification test). Three out of 10 clones had a 98 bp sequence in the cDNA insert (FIG. 1c). After subcloning into the pT7T3 plasmid, this insert was used as a radioactive probe for rescreening the same library, and 15 clones were isolated from the library of one million independent clones with cDNA inserts.

The cDNA clones obtained contained variable internal sequences, in addition to the variable 5' and 3' ends. The clones were grouped by the presence of certain sequences, which were identified as introns based on the presence of termination signals in the coding frame. These clones may be derived from the unspliced or partially spliced mRNA. A repetitive sequence was found downstream of the coding region.

Figure 2:
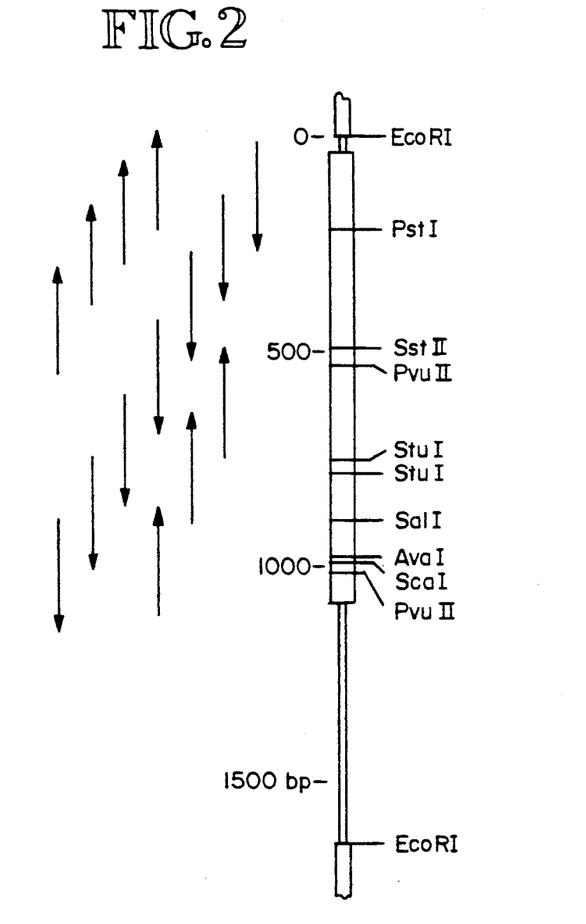
FIG. 2 illustrates the restriction map for cDNA clone (FY-59-5) encoding human A transferase, and the sequencing strategy. The protein coding region is represented by the dotted box and the non-coding regions by the closed bar. The arrows beneath the cDNA indicate direction and extent of sequencing.

Eco RI cDNA inserts were subcloned into the Eco RI site of pT7T3 plasmid or Phagescript SK for detailed analysis. The restriction map of one of the clones, FY-59-5, is shown in FIG. 2. Several other clones show variable mapping due to the presence of intron sequences in addition to variable 5'- and 3'-ends. Several deletion constructs were prepared for sequencing. Sequencing was performed for both strands for the entire coding sequence (FIG. 2).

cDNA clone FY-59-5 has a long coding sequence of 1062 bp (FIG. 3), which encodes a protein of MW 41,000. The first methionine codon appears to be the initiation codon. The amino acid composition of the soluble form of A transferase is in close agreement with the one deduced from the corresponding nucleotide sequence. As discussed above, the MW of N-glycanase-treated A transferase was found to be 34,000, which is in agreement with the value deduced from the nucleotide sequence. All peptides sequenced from the purified A transferase were accounted for, and were nearly identical to the predicted amino acid sequences. Thus, the obtained cDNA clone encodes the 41,000MW protein which was described above as the histo-blood group A transferase.

The N-terminus of the soluble form of purified A transferase begins with the alanine at position 54. A hydrophobic region spanning 21 amino acids precedes this N-terminus and appears to be the transmembrane region of the membrane-bound form of A transferase. A proline-rich region (9 out of 60) follows the hydrophobic region. An N-glycosylation site appears to be located at position 112 (N-T-T). The remaining long C-terminal portion is moderately hydrophilic.

Based upon hydrophobicity plot analysis, the A transferase consists of three domains: a short N-terminal, a hydrophobic transmembrane, and a long C-terminal domain. Since the purified soluble form of this enzyme is catalytically active but lacks the N-terminal and hydrophobic domains, the long C-terminal domain appears to contain the catalytic domain.

Southern hybridization was performed to analyze for restriction fragment length polymorphisms (RFLP) among DNAs from sources with differing ABO blood group antigens. In order to detect the A transferase mRNA, Northern hybridization experiments were performed. Multiple bands were detected in RNAs from cell lines of A, B, AB, and even O phenotype. Thus, the sequences of ABO genes appear to be essentially very similar.

Figure 4:
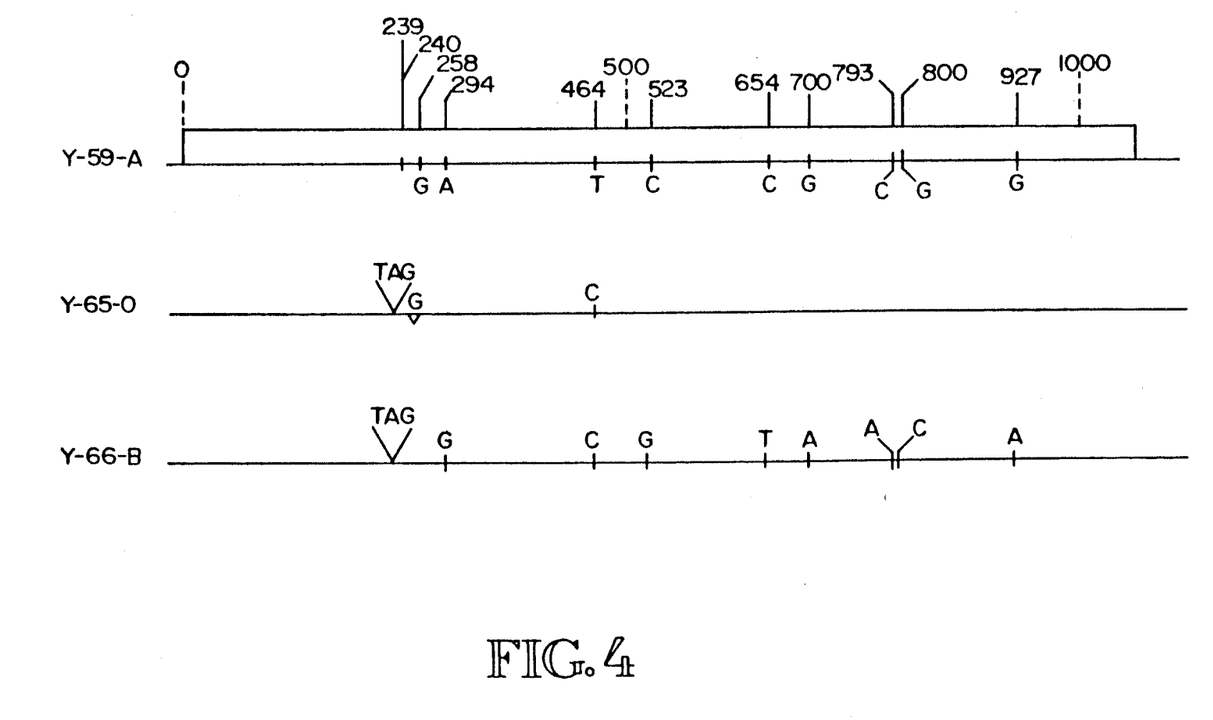

The present invention also provides isolated DNA molecules, including genomic DNA and cDNA, encoding histo-blood group B glycosyltransferase and encoding a protein product, if any, of a histo-blood group O gene. Histo-blood group B glycosyltransferase, also known as UDP-Gal:Fuc$\alpha$1→2Gal$\alpha$1→3Gal transferase, catalyzes the transfer of $\alpha$1→3 Gal to substrates such as Fuc$\alpha$1→2Gal$\beta$1→R (H antigen). No similar transferase activity is associated with the O phenotype. Using the cloning strategies and oligonucleotide probes based on the partial amino acid sequence described above, a B allelic cDNA clone (FY-66-B) was prepared from the human colon adenocarcinoma cell line, SW 147 (available from ATCC), and an O allelic cDNA clone (FY-65-O) from the human colon adenocarcinoma cell line, Colo 205 (available from ATCC). The nucleotide sequence of FY-66-B and FY-65-O are compared to FIG. 4 with that for FY-59-A.

Because polymorphism of ABO phenotypes is known to exist, it will be evident to one skilled in the art that variants in the ABO genes occur. Variants may be isolated by the procedures described herein for representative ABO genes and may be identified based upon the type of antigen expressed by the cell, the specific enzymatic activity detected, and/or other methodology such as that involving hybridization. The term "isolated DNA molecule" as used herein includes both the representative ABO genes described above and variants of these genes. DNA molecules may also be isolated which do not encode the protein products of the A, B, and O genes, but which are capable of specifically hybridizing with a DNA molecule encoding the A, B, and O gene products, respectively.

Based upon the ABO sequence information and material described above, nucleotide probes may be produced, e.g., by PCR amplification, and used for DNA or RNA diagnostic procedures (Landegren et al., Science 242:229, 1988) involving the histo-blood group glycosyltransferases. Differences in the sequences of A, B, and O genes permit preparation of probes selective for these genes. It will be evident to one skilled in the art that the probes may comprise a nucleotide sequence derived from DNA encoding the gene product, or a portion of such DNA. Oligodeoxynucleotides may be synthesized (Tan et al., Cold Spring Harbor Symp. Quant. Biol., Vol. 47, p. 383) or prepared with a DNA synthesizer, e.g., an Applied Biosystems DNA Synthesizer 380B.

Procedures of the present invention employing the nucleotide probes, versus antibodies, permit a higher degree of accuracy and increased sensitivity. Applications of such nucleotide probes include blood group ABO typing, which is useful for blood transfusions, organ transplantations and forensic medicine. In forensic applications, samples that have been stored for years, e.g., a piece of hair, a spot of body fluid or blood, or tissue sections, could by utilized for identification of the histo-blood group.

Suitable methods for determining histo-blood group ABO status by use of nucleotide probes include DNA hybridization. For example, to detect histo-blood group ABO status, at least two DNA probes are prepared. In one embodiment, one of the probes ("A probe") comprises a nucleotide sequence derived from DNA encoding histo-blood A glycotransferase and another probe ("B probe") comprises a nucleotide sequence derived from DNA encoding histo-blood group B transferase. DNA from a patient is isolated. The hybridization of the probes with DNA isolated from a patient may be performed with both probes present or with each probe incubated with separate aliquots of the patient's DNA.

For example, in one embodiment, a single aliquot of the patient's DNA is incubated with the two DNA probes described above (A and B probes) under conditions permitting hybridization. If hybridization has occurred, a pattern of hybridization is detected which is diagnostic for the presence of histo-blood group A status or B status. The absence of a pattern is diagnostic for the presence of histo-blood group O status. The step of detecting may be performed by use of a reporter group, bound to the probe, to a molecule that reacts with the probe, or to a second molecule that reacts with the first molecule. Suitable reporter groups include radioisotopes, fluorophores, enzymes, luminescers, and dye particles. Each DNA probe may contain a different reporter group.

In another embodiment for determining histo-blood group ABO status by DNA hybridization, the probes described above (A and B probes) are incubated separately with different aliquots of a patient's DNA. For example, a first aliquot of the DNA is incubated with the A probe and a second aliquot is incubated with the B probe. A pattern of hybridization of the first aliquot is diagnostic for the presence of histo-blood group A status and a pattern of hybridization of the second aliquot is diagnostic for the presence of B status. The absence of a pattern of hybridization of both first and second aliquots is diagnostic for the presence of O status. The discussion above regarding the step of detecting is applicable here as well.

It may be desirable for either method involving hybridization to cleave the DNA isolated from a patient to produce DNA fragments. Such cleavage may be performed by digestion of the DNA with at least one restriction endonuclease. In addition, it may be desirable for either method involving hybridization to amplify the DNA isolated from a patient. Such amplification may be performed using PCR methodology. Oligodeoxynucleotide hybridization methodology and application of PCR are well known in the art (e.g., Miyada et al., *Methods in Enzymology.* Vol. 154, P. 94; Bos et al., *Nature* 327:293, 1987).

Another suitable method for determining histo-blood group ABO status involves distinguishing DNA fragments by size. For example, DNA is isolated from a patient and cleaved with at least one restriction endonuclease to produce two or more DNA fragments. The fragments are separated by size and histo-blood group ABO status is determined from the detection of the presence of DNA fragments unique to histo-blood group A, or B or D status. For example, allele-specific restriction sites include Nar I and Alu I. These restriction enzymes when combined with PCR yield allele-unique fragments.

Another aspect of the present invention based upon the cloning and characterization of the A and B transferase genes is the preparation of DNA constructs and recombinant plasmids. As noted above, the term "DNA constructs" as used herein comprises segments of DNA which are combined and juxtaposed in a manner which would not otherwise exist in nature. More specifically, DNA constructs may comprise a DNA sequence encoding histo-blood group A, or B, glycosyltransferase in which there has been one or more deletions, substitutions, additions, and/or insertions, relative to "isolated" DNA sequences. A portion of the DNA sequence may be derived from a genomic or cDNA clone. The DNA described herein may include a suitable promoter.

Within a preferred embodiment of the present invention, recombinant plasmids capable of integration into a host cell comprise a promoter followed downstream by a DNA sequence encoding histo-blood group A, or B, transferase, which in turn is followed downstream by a polyadenylation signal. The DNA sequence may be cDNA or genomic DNA. The plasmids may be used to stably transfect (transform) cells and thereby establish a host cell (*Current Protocols in Molecular Biology.* Vol. 1 & 2, Wiley Interscience). One embodiment of a method for producing histo-blood group A, or B, glycosyltransferase comprises introducing into a host cell an isolated DNA molecule encoding a histo-blood group A, or B, glycosyltransferase, or a DNA construct comprising a DNA sequence encoding histo-blood group A, or B, glycosyltransferase. The host cells are grown in an appropriate medium and the protein product encoded by the isolated DNA molecule or the DNA construct produced by the host cell is isolated. Preferred host cells include mammalian cells. Particularly preferred host cells include COS-1 cells. Suitable methods for introducing cloned DNA sequences into cultured mammalian cells include calcium phosphate mediated transfection (e.g., Wigler et al., *Cell* 14:725, 1978; Corsaro and Perason, *Somatic Cell Genetics* 7:603, 1981; Graham and Van der Eb, *Virology* 52:456, 1973). It will be evident to one skilled in the art that it is not necessary to use the entire sequence when producing recombinant A or B transferase proteins.

Another aspect of the present invention provides a method for suppressing tumor growth in a bacterial cell which contains a DNA sequence encoding histo-blood group A glycosyltransferase. The bacterial cell is then introduced into a patient, thereby enriching the bacterial flora to A antigen. This enrichment stimulates a humoral immune response to the patient's tumor. Suitable nonpathogenic bacteria include strains of Lactobacillus. A bacterial cell expressing A antigen may be established by introducing a DNA sequence encoding histo-blood group A glycosyltransferase.

The following examples are offered by way of illustration and not by way of limitation.

EXAMPLES

Example 1

Purification of Human UDP-GalNAc: Fucα1→Gal α1→3-N-acetylgalactosaminyltransferase A. Determination of e-GalNAc Transferase Activity (1) Glycolipids.

The α-/GalNAc transferase activity was determined in reaction mixtures containing 10 mM Tris buffer (pH 7.4), 25 μg $H_1$ or $H_2$ type 2 chain substrate glycolipid, 2 μmol $MnCl_2$, 0.5 μmol CDP-choline, 40 μg Cutscum, 11 nmol UDP[$^{14}$C]-GalNAc (22,816 cpm/nmole; labeled from Amersham and unlabeled from Sigma Chemical Co.), and enzyme preparations as described below, in a total volume of 100 μl. Radioactive glycolipid products were located by autoradiography, scraped from the plate, and counted using a liquid scintillation counter. Identification of the reaction produce was assessed by high-performance thin-layer chromatography (HPTLC) immunostaining using Anti-A MAbs with well-characterized specificity, as previously described by Clausen et al. (*J. Immunol.* 136:326–330, 1986).

(2) 2-Fucosyllactose.

Transferase activity was determined in the same reaction mixture as for glycolipid assay, but with omission of Cutscum and a lower specific activity of sugar nucleotide (4,000 cpm/nmole). The accepter substrate 2- fucosyllactose (2'FL) was used in concentrations of 5-10 mM, and product determined by scintillation counting after Dowex-1 formic acid cycle chromatography.

B. Isolation to Homogeneity

Buffers pH measured at room temperature. Buffer A: 100 mM NaCl, 50 mM cacodylic acid, 2 mM MnCl, 1 mM ethylenediaminetetraacetic acid (EDTA), 1% Triton X-100, pH 6.7. Buffer B: 100 mM NaCl, 50 mM cacodylic acid, 20 mM MnCl, 1 mM EDTA, 0.1% Triton X-100, pH 6.5. Buffer C: 50 mM cacodylic acid, 20 mM MnCl, 1 mM EDTA, 50 μM UDP, 0.1% Triton X-100, pH 7.5. Buffer D: 50 mM cacodylic acid, 2 mM MnCl, 1 mM EDTA, pH 6.5.

Several human enzyme sources were tested, and lung tissue chosen on the basis of apparent high specific activity and the fact that this enzyme activity apparently was mostly soluble. Blood group A and AB lungs (no information on A subgroup status was available) frozen ($-80°$ C.) 24-72 hrs post mortem were used. During purification, glass tubes siliconized by 1% prosil-28 (Thomas Scientific) followed by 30 min heating ($100°$ C.) were used. All steps of purification were performed at $4°$ C.

Step 1

Extraction and purification procedures up to step 4 were carried out with one single lung (1–2 kg) at a time. Thawed tissues were homogenized in $2\times$ vol of buffer A in a one-gallon Waring blender (four 10–20 sec homogenization with 30 sec interval). The crude homogenate was centrifuged for 1 hr at 10,000 rpm in a Beckman JA-10 rotor. The supernatants were further filtered through Whatman No. 1 paper.

Step 2

Sepharose 4B chromatography: Batches of 4 l of supernatant extract were passed over pre-equilibrated ml Sepharose 4B (lot #56F0333 & 56F0377, purchased from Sigma) columns of diameter 30 mm (Biorad) at a flow rate of $\approx 3$ ml/min. The column was washed with 200 ml buffer B and eluted with 100 ml of buffer C, containing 50 μM GDP or UMP as well as 0.2M NaCl did not elute the enzyme activity, but removed other contaminating proteins. The increased washing effect, however, reduced the yield at elution. Fractions containing enzyme activity ($\approx 30$ ml) were pooled, diluted with 50 mM cacodylate buffer (pH 6.0) to a final volume of 50 ml, and adjusted to pH 6.2 with 1M free cacodylic acid. The enzyme with addition of 25% glycerol was stable on ice for several days without significant loss of activity, and could be kept at $-30°$ C. for months without loss of activity.

Step 3

Primary cation exchange (Mono-S HR 5/5) chromatography: The diluted and pH-adjusted Sepharose 4B eluate was applied to a mono-S HR 5/5 column (Pharmacia LKB, Upsala, Sweden) through a 50 m superloop in conjunction with a Pharmacia (Upsala, Sweden) fast pressure liquid chromatography (FPLC) system. The column was equilibrated in buffer D and washed with 20 ml of the same. Elution was obtained by a gradient of 0–0.5M NaCl in buffer D in 23 ml with a flow rate of 1 ml/min. Fractions containing enzyme activity ($\approx 5$ ml) were pooled and 25% glycerol added. At this stage, the enzyme without glycerol was very unstable, but with glycerol it was stable for 24–48 hrs on ice and for weeks at $-30°$ C.

Step 4

Secondary ion exchange (mono-S HR 5/5) chromatography: Pooled fractions from 6–8 individual lung extracts kept frozen after the primary mono-S HR 5/5 column step (step 3) were pooled and diluted with buffer D to 100 ml and reapplied through 2 volumes of a 50 ml superloop to the mono-S column. The chromatography was as described for step 3. This step allowed concentration and removal of glycerol, in addition to some purification as evidenced by the UV (280 nm) elution profile.

Step 5

Reverse phase (proRPC H5/10) chromatography: In order to obtain homogeneous protein free of salt and buffer without significant loss, the eluate ($\approx 5$ ml) of secondary mono-S chromatography (step 4) were diluted with 0.1% trifluoroacetic acid (TFA) to a final volume of 10 ml and pH adjusted with TFA to 2.5. The sample was applied in a 10 ml superloop to a proRPC H5/10 column (Pharmacacia LKB, Upsala, Sweden) in conjunction with a Pharmacia FPLC system. This column was washed with 10 ml 0.1% TFA and eluted with a gradient of 0–80% acetonitrile in 0.1% TF in 40 ml at a flow rate of 0.3 ml/min. Fractions were pooled based on UV (280 nm) absorption and sodium dodecyl sulfate polyacrylamide gel electrophoresis (SDS-PAGE) profile.

EXAMPLE 2

Determination of Amino Acid Composition and N-terminal Sequence

An enzyme preparation taken through step 5 of Example 1 from a total of 6–8 lungs (equivalent of 10–12 kg of tissue) was used. Fractions containing the homogeneous A transferase protein were pooled and lyophilized in a Speed Vac concentrator in siliconized plastic microfuge tubes. Protein was hydrolyzed at $110°$ C. for 24 hours or 74 hrs in 6N HCl under vacuum and applied to an amino acid analyzer (Hitachi L-8500).

TABLE 1

| | Amino Acid Compositions (moles/ mole enzyme)[a] | | |
|---|---|---|---|
| | 24 hr hydrolysis | 72 hr hydrolysis | mean value[b] |
| Asp/Asn | 22.41 | 22.44 | 22.43 |
| Thr | 16.25 | (15.57) | 16.25 |
| Ser | 16.25 | (13.26) | 14.96 |
| Glu/Gln | 38.18 | 37.91 | 38.05 |
| Gly | 21.25 | 21.18 | 21.22 |
| Ala | 17.78 | 17.78 | 17.78 |
| Val | 31.93 | 30.94 | 31.44 |
| Cys/2 | 0.75 | (0.10) | 0.75 |
| Met | 3.37 | (2.89) | 3.37 |
| Ile | 9.79 | 9.32 | 9.56 |
| Leu | 30.60 | 29.92 | 30.26 |
| Tyr | 13.43 | 12.58 | 13.01 |
| Phe | 16.18 | 16.39 | 16.29 |
| Lys | 13.74 | 13.91 | 13.83 |
| His | 10.54 | 10.91 | 10.73 |
| Arg | 21.96 | 22.00 | 21.98 |
| Pro | 16.25 | 18.67 | 17.46 |
| Trp | ND | ND | ND |

TABLE 1-continued

| Amino Acid Compositions (moles/ mole enzyme)[a] | | |
|---|---|---|
| 24 hr hydrolysis | 72 hr hydrolysis | mean value[b] |
| Total | | 299.37 |

[a]Amino acid composition is expressed as moles of residue per mole of A transferase (estimated MW 34,000, excluding carbohydrate moiety).
[b]Unstable amino acids such as Thr, Ser, Cys, and Met were taken from the 24 hr hydrolysis values.

Apparently, 30 μg of the A transferase was carboxymethylated after reduction, and further purified by TSK G2000SW column. The N-terminal sequence of this component was determined by automated Edman degradation using a sequencer. The A transferase was also degraded by Achromobacter endolysyl peptidase, the peptide released was fractioned on high-pressure liquid chromatography (HPLC) through TSK G2000SW sXL column, and various peptides (K1 through K9) were separated. Each peptide was sequenced as described above.

TABLE 2

Amino Acid Sequence of N-terminal Region and Various Peptides Released by Achromobacter Endolysyl Peptidase and by Cyanogen Bromide Cleavage from the A Transferase[1]

N-terminal sequence from intact A enzyme
    AVREPDHLQRVSLPRMVYPQXKVL Peptides released by Achromobacter endolysyl peptidase

| K1 | VLTPQXK |
| K2 | YLLRHKPTK |
| K3 | LRFTAVPK |
| K4 | AVREPDHLQRVSLPRMVYPQXK |
| K5 | DFMVGHRVHYYVFTXXPAAVPRVTL------ |
| K7 | VLSPEYLWDQXLLGWPAVLXK |
| K8 | dEGhFYYLGGFFGGSVQEVQRLTRAQ/CXQAMMVDQAnGIEAV------ |
| K9 | rVLVVT------ |

Peptides released by cyanogen bromide degradation

| M4: | VYPQPKVLTPCRKDVLVVTPWLAPIVWEGTFNIDILNeqf------ |
| M5: | EFRDHVGVEILTPLFGTLHPgFYXeXXEAF------ |
| M6: | VDQANGIEAV------ |
| M7: | VGHRVHYYVFTDQPAAVPRVTLGTGRQLSVLEvrAYy------ |
| M8: | ISDFCERRFLSEVDVLVCVD------ |
| M9: | AVREPDHLQRVSLPRM |

Combined N-terminal sequence

|----------intact enzyme------------|

|--------------- K4 -------------|--- K1 ---|---------------K9---------------→

AVREPDHLQRVSLPRMVYPQPKVLTPCRKDVLVVTPWLAPIVWEGTFNIDILNeqf

|---------M9-----------|-------------------- M4 ------------------------→

[1]X, unidentifiable residue; lower case letter, low yield of the amino acid residue having the corresponding upper case designation.

rescence immunoassay (PCFI), fluorescent staining of blood group A cells with high A transferase activity (MKN-45) and immunoprecipitation of transferase activity. Controls included various A glycolipids (prepared as described by Clausen et al., *Biochemistry* 25:7075-7085, 1986) and cell lines with no A or B transferase activity (Colo205). Isotype and subclass were determined by PCFI using goat anti-mouse fluorescein isothiocyanate (FITC)-conjugated antibodies, as well a by the Ochterlony method of using rabbit anti-mouse antibodies (Boehringer Mannheim Biochemicals). MAbs were used as tissue culture supernatants unless otherwise indicated. Antibodies were purified on a protein A Sepharose 4B column (pH 9.0) eluted with 100 mM citrate buffer (pH 4.2), and dialyzed against 20 mM Tris buffer (pH 7.4).

B. PCFI Screening

Approximately 50 μg of purified transferase (prepared as described in Example 1) was mixed with 1 ml of 0.5% (w/v) Fluoricon Carboxyl-Polystyrene Assay Particles (0.86 μm, Pandex) and covalently coupled by adding solid 1-ethyl-3[3-dimethyl-aminopropyl] carbodiimide to give a final concentration of 1 mg/ml. Controls for reactivity with carbohydrates included beads similarly coated with salivary or ovarian cyst mucins (a generous gift from Dr. Elvin Kabat), as well as beads coated with A-active glycolipids as described previously by Clausen et al., *Molec. Immun.* 25:199-204, 1988. After vortexing, the mixture was incubated at room temperature for 1-2 hours. The microparticles were then centrifuged (3,000×g, 10 min.), washed with phosphate-buffered saline (PBS), blocked with either bovine serum albumin (BSA)/PBS 5% or human serum (1:10 dilution), and brought to final volume of 0.25% w/v in PBS. Antigen-coated particles were then diluted 1:10 in BSA-coated particles (similar procedure) to give

EXAMPLE 3

Preparation and Characterization of MAbs Directed to Human Histo-Blood Group A Transferase A. Generation of Mabs Production of three Mabs, WKH-1, -2, and -3, directed to human blood group A glycosyltransferase, was, obtained by immunization of 3-month-old BALB/c mice. Mice were immunized with A transferase (prepared as described in Example 1) emulsified in Ribi's adjuvant (monophosphoryl lipid A+ halose dimycolate) by intraperitoneal injection 4 times (3 week interval), with approximately μg of transferase per injection. Spleen cells were fused with NS-1 myeloma cells 3 days after the last immunization, and hybridomas were cloned by limiting dilution at least 3 times. Hybridomas were screened by particle-concentrated fluoa final particle concentration of 0.225% BSA particles and 0.025% transferase particles. Twenty μl of BSA-transferase or BSA-coated particles were distributed in 96-well Epicon assay plates (Pandex) with a 0.2 μm filter. The automated particle concentrated fluorescence immunoassay screen machine (Pandex) (as described in Jolley et al., *J. Immunol. Meth.* 67:21–35, 1984) performed the following steps sequentially by vacuum suction through the 0.2 μm filter in the bottom of each well and distribution of buffers through an 8-channel pump: incubation for 10 min. with 50 ul of Mab culture supernatant, washing with PBS, incubation for 10 min. with 25 μl of affinity-purified goat anti-mouse Ig FITC-conjugated antibody (1:200, Pandex), washing with PBS, and reading at 485 mm/535 nm after final suction centering and concentrating antigen-coated particles in the bottom of wells.

C. Immunostaining of Cell Lines and Tissues

Cells were grown in media according to American Type Culture Collection (ATCC) guidelines, harvested by rubber policeman, and air-dried onto 10-well microslides (Carbon Scientific, Peokone, Ill.) for 2 hours. Slides were "fixed" in ice-cold acetone for 10 minutes and allowed to dry. Cells were incubated with primary antibody for 45 minutes at 37° C., washed with PBS, and incubated with fluorescein-conjugated rabbit anti-mouse antibody (Dakopatts, Denmark) for 30 minutes at 37° C. Similarly, human buccal mucosal tissues, salivary glands, and human intestine obtained at surgery were quick-frozen in isopentane precooled with dry ice, sectioned with a cryostat after embedding in Tissue-Tek ® (Miles Scientific), and processed immediately for immunostaining. Sections were air-dried briefly and "fixed" in acetone and immunostained as described "fixed" in acetone and immunostained as described for cell lines, except primary antibodies were incubated for 4 hours or overnight at 4° C.

Slides were examined in a Zeiss fluorescence microscope using epi-illumination. The microscope was equipped with FITC interference filters and a 200W Mercury lamp. For control of the staining, primary antibody was replaced with PBS or MAbs of other specificities but with the same isotype as the test antibody. Staining with the MAbs was also performed after "fixation" with paraformaldehyde or glutaraldehyde on air-dried slides and on cells grown as tumors in nude mice, which were fixed, paraffin-embedded, and sectioned. In the case of colonic tissues, sections were stained by avidin-biotin-peroxidase complex as previously described by Orntoft et al., *Lab. Invest.* 58:576–583, 1988.

D. Immunoprecipitation of A Transferase Activity

One mg of affinity-isolated goat anti-mouse IgG (Boehringer Mannheim Bio-chemicals) was added to 10 ml of 1% Fluoricon Polystyrene Assay Particles (0.85 μm, Pandex) in PBS. After two hours at room temperature, the suspension was centrifuged (3,000×g) for 10 minutes, blocked with 3% BSA in PBS and resuspended to a final concentration of 1% w/v. Goat anti-mouse particles were mixed with MAb hybridoma supernatants in a 1:5 ratio, incubated at 4° C. for 15 minutes, and centrifuged (3,000×g) for two minutes. The beads were washed with Buffer A (50 mM Tris buffer [pH 7.4], 100 mM NaCl, 20 mM $MnCl_2$, 1 mM ethylenediaminetetraacetic acid, 0.1% Titron X-100, and 3% BSA), and resuspended in Buffer A to a concentration of 1%. Particles were added to enzyme samples to a concentration capable of binding to twice the amount of A transferase present (about 100 μl particles for 500 μl concentrated plasma). After 30 minutes at 4° C., the particles were centrifuged at 3,000×g for two minutes and the supernatant was assayed for remaining enzyme. The precipitated particles were washed twice with Buffer A, resuspended in 50 μl wash buffer, and assayed for enzyme activity. The transferase used was either purified or semipurified from human blood group A lungs, or from blood group A1, $A_2$, B or O plasma concentrated 10× by 30–50% ammonium sulfate precipitation followed by concentration in an Amicon stirred cell membrane concentrator. Fucosyltransferase was from a Triton CF-54 homogenate of Colo205 cells after centrifugation at 100,000×g for one hour.

E. Inhibition of Transferase Activity by MAbs

Purified anti-A transferase MAbs, irrelevant MAbs with the same isotype, commercially obtained $IgG_1$ myeloma standard, or 20 mM Tris buffer (pH 7.4) were added to transferase preparations and incubated at 4° C. for 30 minutes. The enzyme activity of this mixture was then measured by incubation with reaction mixture at 37° C. for 10 or 30 minutes.

EXAMPLE 4

Cloning and Characterization of DNA Complementary to Histo-Blood Group A Transferase mRNA

A. Preparation of Synthetic Oligodeoxynucleotide Probes According to Partial Amino Acid Sequence Data Based on amino acid sequences of a few peptides released on Achromobacter endolysyl peptidase treatment or cyanogen bromide cleavage (described in Example 2), synthetic oligodeoxynucleotides were prepared with an Applied Biosystems DNA Synthesizer 380B.

B. RNA and DNA Preparation

Total RNA was prepared by the guanidine-HCl method (e.g., Winter et al., *J. Cell Biol.* 101:175–181, 1985; *Proc. Natl. Acad. Sci. U.S.A.* 82:7575–7579, 1985). In brief, cell pellets were homogenized in guanidine-HCl solution and ethanol-precipitated twice. After resuspension in a saline/SDS mixture, RNA was extracted with phenol and Savages mixture (chloroform-/isoamyl alcohol, 24:1), followed by ethanol precipitation. The poly A+ fraction was selected by oligo-dT cellulose column chromatography (Maniatis et al., *Molecular Cloning: A Laboratory Manual*, 1982, Cold Springs Harbor Laboratory, New York. Genomic DNA was purified by digesting the tissues with proteinase K in the presence of SDS and EDTA, followed by extraction with Seavag's mixture and ethanol precipitation (Id.)

C. cDNA Libraries

All reagents and enzymes for cDNA synthesis were from the Promega cDNA synthesis kit and were used as per the manufacturer's instructions. cDNA was synthesized with MKN45 poly A+ RNA by the method of Gubler and Hoffman (*Gene* 25:263–269, 1983) using a random hexamer, instead of oligo-dT, as a primer. The cDNA was ligated with a phosphorylated Eco RI linker, digested with Eco RI, and electrophoresed on 1% agarose gel. The cDNA was size-selected (>1.3 bkb) and recovered from the gel by the PI method (Volgelstein and Gillespie, *Proc. Natl. Acad Sci. U.S.A.* 76:615, 1979), then ligated to the dephosphorylated Eco RI arms of the λgt10 vector. The ligated DNA was packaged in vitro with Stratagene's Giga Pack Gold packaging extract.

D. Screening of λgt10 Library

1. PCR Presence Test (cDNA) and PCR Identification Test (DNA From the Candidate Phage Clones)

The polymerase chain reaction (PCR) (Saiki et al., *Science* 230:1350–1354, 1985; Saiki et al., *Science* 239:487–491, 1988) was performed using two degenerate synthetic oligos FY-1 and FY-2 (Fig. 1) as primers with TAq DNA polymerase. The reagents and enzyme were purchased from Perkins Elmer Cetus. Thirty-five cycles of DNA polymerization (72° C.; 3 min.) denaturation (94° C.; 2 min) and annealing (50° C.; 2 min.) were performed on the cDNA of MKN45 poly A+ RNA. The final 72° C. incubation was for 10 minutes. The product was electrophoresed on a 5% polyacrylamide gel and electrotransferred onto a Nylon membrane (Amersham). The membrane was baked at 80° C. under vacuum and probed for the internal sequence with a $^{32}$P-kinase-labeled oligodeoxynucleotide probe (FY-3). Presence of a hybridized band of expected length was considered a positive test.

2. Screening

Amplified fragment (98 bp) from the PCR presence test was gel-purified and used to screen the cDNA library. The positive plaques were cloned after the screening and DNA was prepared and analyzed by the PCR identification test.

E. Northern and Southern Hybridizations

Fifty µg RNAs or 5 µg poly A+ RNAs were electrophoresed through a denaturing formaldehydeagarose gel and transferred onto a Nylon membrane. Eight µg genomic DNA was digested overnight with the appropriate restriction endonuclease and loaded onto a 1% agarose gel. After electrophoresis, the gels were denatured (30 min.) in 0.5N Na)H and 1.5M NaCl, neutralized (30 min., 2×) in 0.5M Tris-HCl (pH 7.5) 3M NaCl, and the DNA was transferred onto a Nylon membrane by capillary action (Maniatis et al., *Molecular Cloning: A Laboratory Manual*, 1982, Cold Springs Harbor Laboratory, New York). Both Northern and Southern filters were prehybridized in 50% formamide, 5× SSPE, 5× Denhardt's, and 0.1% SDS solution at 42° C. for two hours and then hybridized overnight at 42° C. with a $^{32}$P random primed-labeled (Feinberg and Vogelstein, *Anal. Biochem* 132:6, 1983; *Anal. Biochem.* 137:266, 1984) probe from FY-59-5 insert. Filters were washed in 2× SSC, 0.1% SDS at room temperature three times and then in 1× SSC, 0.1% SDS at 68° C. for one hour. Final wash was in 0.1× SSC, 0.1% SDS at 68° C. for one hour.

F. Subcloning and Restriction Enzyme Mapping

DNA from the phage clones was digested with Eco RI and ligated with dephosphorylated Eco RI arms of pT7T3 plasmid (Pharmacia) or Phagescript SK (Stratagene). After DNA transformation of XL-1 Blue strain bacteria, the clones with insert were screened by color selection with IPTG and X-gal. Restriction enzymes were obtained from BRL or New England Biolabs.

G. DNA Sequencing

Dideoxynucleotide termination sequencing reactions (Sanger et al., *Proc. Natl. Acad. Sci. U.S.A.* 74:5463–5467, 1977) were performed with single-strand DNA of Phagescript clones or pT7T3 clones obtained by super-infection with helper phage. M13 universal primer and several synthetic oligodeoxynucleotide primers were used. The sequencing strategy is shown in FIG. 2. DNA sequencing was done using Sequenase (United States Biochemical Corp.), Klenow enzyme (BRL kilobase system), and, for ambiguous regions, Taq DNA polymerase (Promega). IBI Pustell Sequence Analysis Software (MS-DOS version) was used for sequence analysis.

From the foregoing, it will be evident that, although specific embodiments of the invention have been described herein for purposes of illustration, various modifications may be made without deviating from the spirit and scope of the invention.

We claim:

1. A purified histo-blood group A glycosyltransferase having the following characteristics:
   a) molecular weight of approximately 40,000 as measured by sodium dodecyl sulfate-polyacrylamide gel electrophoresis; and
   b) specific activity of at least approximately 5 international units per mg of protein.

2. The enzyme of claim 1 wherein said enzyme is derived from human cells.

3. An antibody which is capable of binding to a protein epitope on a histo-blood group A glycosyltransferase according to claim 1.

4. The antibody of claim 3 wherein the antibody is a monoclonal antibody.

5. A monoclonal antibody produced by a hybridoma formed by the fusion of cells from a myeloma line and spleen cells from an animal previously immunized with a histo-blood group A glycosyltransferase according to claim 1.

6. The cell line WKH-1, as designated by ATCC No. NB 10207.

7. A monoclonal antibody produced by the cell line of claim 6.

8. A monoclonal antibody produced by a hybridoma equivalent to the hybridoma of claim 6, wherein said antibody competitively inhibits the formation of an immunocomplex between the antibody of claim 7 and histo-blood group A transferase.

* * * * *

UNITED STATES PATENT AND TRADEMARK OFFICE
CERTIFICATE OF CORRECTION

PATENT NO. : 5,068,191
DATED : November 26, 1991
INVENTOR(S) : Henrik Clausen et al.

It is certified that error appears in the above-identified patent and that said Letters Patent is hereby corrected as shown below:

In column 18, claim 6, line 51, please delete "NB" and substitute therefor -- HB --.

Signed and Sealed this

Fifteenth Day of June, 1993

Attest:

MICHAEL K. KIRK

Attesting Officer

Acting Commissioner of Patents and Trademarks

UNITED STATES PATENT AND TRADEMARK OFFICE
CERTIFICATE OF CORRECTION

PATENT NO.  :   5,068,191

DATED       :   November 26, 1991

INVENTOR(S) :   Henrik Clausen et al.

It is certified that error appears in the above-identified patent and that said Letters Patent is hereby corrected as shown below:

In column 1, line 5, immediately before the Technical Field, please insert:

ACKNOWLEDGEMENT OF GOVERNMENT SUPPORT
This invention was made with government support under Grant 5R35CA42505 awarded by the National Cancer Institute. The government has certain rights in the invention.

Signed and Sealed this

Twenty-eighth Day of September, 1993

Attest:

BRUCE LEHMAN

Attesting Officer

Commissioner of Patents and Trademarks